US006241691B1

(12) United States Patent
Ferrera et al.

(10) Patent No.: US 6,241,691 B1
(45) Date of Patent: *Jun. 5, 2001

(54) COATED SUPERELASTIC STENT

(75) Inventors: David A. Ferrera, San Francisco; Peter Wilson, Foster City, both of CA (US)

(73) Assignee: Micrus Corporation, Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/227,982

(22) Filed: Jan. 8, 1999

Related U.S. Application Data

(63) Continuation of application No. 09/143,507, filed on Aug. 28, 1998, now abandoned, which is a continuation-in-part of application No. 08/986,004, filed on Dec. 5, 1997, now abandoned.

(51) Int. Cl.[7] ....................................................... A61B 5/00
(52) U.S. Cl. ......................... 600/585; 623/1.18; 623/1.22
(58) Field of Search ..................................... 600/585, 434, 600/435; 604/104; 606/191, 194, 108; 623/1, 11, 12, 1.1, 1.12, 1.13, 1.15, 1.18, 1.22, 1.34, 1.42, 1.45, 1.47

(56) References Cited

U.S. PATENT DOCUMENTS

| 1,341,052 | 5/1920 | Gale . | |
|---|---|---|---|
| 1,667,730 | 5/1928 | Green | 75/84 |
| 2,078,182 | 4/1937 | MacFarland | 75/84 |
| 2,549,335 | 4/1951 | Rahthus | 59/83 |
| 3,334,629 | 8/1967 | Cohn | 128/325 |

(List continued on next page.)

FOREIGN PATENT DOCUMENTS

| 4102550 A1 | 8/1991 | (DE) . |
|---|---|---|
| 0 183 372 A1 | 6/1986 | (EP) . |
| 0 278 937 | 8/1988 | (EP) . |
| 0 382014 A1 | 8/1990 | (EP) . |
| 0 518 704 A1 | 12/1992 | (EP) . |
| 0 627 201 A1 | 12/1994 | (EP) . |
| 592182 | 7/1925 | (FR) . |
| 2 066 839 | 7/1981 | (GB) . |
| WO92/14408 | 9/1992 | (WO) . |
| WO94/16629 | 8/1994 | (WO) . |
| WO95/18585 | 7/1995 | (WO) . |
| WO95/21592 | 8/1995 | (WO) . |
| WO97/48351 | 12/1997 | (WO) . |

OTHER PUBLICATIONS

Copy of International Search Report Relating to PCT/US97/10882 Dated Nov. 6, 1997.
Copy of International Preliminary Examination Report Relating to PCT/US97/10882 Dated Aug. 10, 1998.
Christos A. Athanasoulis, M.D., The New England Journal of Medicine, May 15, 1980, "Therapeutic Applications of Angiography" pp. 1117–1725 (1 of 2).

(List continued on next page.)

Primary Examiner—Cary O'Connor
Assistant Examiner—Charles Marmor, II
(74) Attorney, Agent, or Firm—Fulwider Patton Lee & Utecht, LLP

(57) ABSTRACT

The coated superelastic stent is formed from a tube of collagen having an inner structure of a micro-cable made of strands of a material exhibiting superelasticity or shape memory properties, such as nickel-titanium, and includes a strand of radiopaque material, such as platinum or gold, in order to provide a radiopaque marker during interventional therapeutic treatment or vascular surgery. The collagen tube can be loaded with a therapeutic agent for treatment of the desired site in the vasculature.

35 Claims, 10 Drawing Sheets

U.S. PATENT DOCUMENTS

| | | | |
|---|---|---|---|
| 3,485,234 | 12/1969 | Stevens | 128/2 |
| 3,649,224 | 3/1972 | Anderson et al. | 29/182.5 |
| 3,868,956 | 3/1975 | Alfidi et al. | 128/345 |
| 4,161,952 | 7/1979 | Kinney et al. | 128/786 |
| 4,494,531 | 1/1985 | Gianturco | 128/1 R |
| 4,512,338 | 4/1985 | Balko et al. | 128/1 R |
| 4,553,545 | 11/1985 | Maass et al. | 128/343 |
| 4,629,458 | 12/1986 | Pinchuk | 623/1 |
| 4,638,803 | 1/1987 | Rand | 128/325 |
| 4,655,771 | 4/1987 | Wallsten | 623/1 |
| 4,670,286 | 6/1987 | Nyllas et al. | 427/2 |
| 4,682,607 | 7/1987 | Vaillancourt et al. | 600/585 |
| 4,718,907 | 1/1988 | Karwoski et al. | 623/12 |
| 4,732,152 | 3/1988 | Wallstén et al. | 128/343 |
| 4,748,986 | 6/1988 | Morrison et al. | 600/585 |
| 4,768,507 | 9/1988 | Fischell et al. | 128/303 R |
| 4,795,458 | 1/1989 | Regan | 623/1 |
| 4,798,606 | 1/1989 | Pinchuk | 623/1 |
| 4,800,882 | 1/1989 | Gianturco | 128/343 |
| 4,813,925 | 3/1989 | Anderson, Jr. et al. | 604/8 |
| 4,820,298 | 4/1989 | Leveen et al. | 623/1 |
| 4,830,003 | 5/1989 | Wolff et al. | 128/343 |
| 4,850,960 | 7/1989 | Grayzel | 604/53 |
| 4,856,516 | 8/1989 | Hillstead | 128/343 |
| 4,873,978 | 10/1989 | Ginsburg | 128/345 |
| 4,922,924 | 5/1990 | Gambale et al. | 600/585 |
| 4,932,419 | 6/1990 | de Toledo | 600/585 |
| 4,950,258 | 8/1990 | Kawai et al. | 604/281 |
| 4,954,126 | 9/1990 | Wallstén | 600/36 |
| 4,957,479 | 9/1990 | Roemer | 604/8 |
| 4,957,501 | 9/1990 | Lahille et al. | 606/200 |
| 4,990,155 | 2/1991 | Wilkoff | 606/191 |
| 4,994,069 | 2/1991 | Ritchart et al. | 606/191 |
| 4,998,916 | 3/1991 | Hammerslag et al. | 604/95 |
| 5,015,253 | 5/1991 | MacGregor | 623/1 |
| 5,019,090 | 5/1991 | Pinchuk | 606/194 |
| 5,025,799 | 6/1991 | Wilson | 600/585 |
| 5,026,377 | 6/1991 | Burton et al. | 606/108 |
| 5,035,706 | 7/1991 | Giantureo et al. | 606/198 |
| 5,037,377 | 8/1991 | Alonso | 600/36 |
| 5,037,391 | 8/1991 | Hammerslag et al. | 604/95 |
| 5,041,084 | 8/1991 | DeVries et al. | 604/43 |
| 5,041,126 | 8/1991 | Gianturco | 606/195 |
| 5,055,101 | 10/1991 | McCoy | 604/95 |
| 5,061,275 | 10/1991 | Wallstén et al. | 623/1 |
| 5,063,935 | 11/1991 | Gambale | 600/585 |
| 5,064,435 | 11/1991 | Porter | 623/12 |
| 5,071,407 | 12/1991 | Termin et al. | 604/104 |
| 5,092,847 | 3/1992 | Pozzo | 604/170 |
| 5,104,404 | 4/1992 | Wolff | |
| 5,108,407 | 4/1992 | Geremia et al. | 606/108 |
| 5,122,136 | 6/1992 | Guglielmi et al. | 606/32 |
| 5,133,731 | 7/1992 | Butler et al. | 606/191 |
| 5,133,732 | 7/1992 | Wiktor | 606/195 |
| 5,141,502 | 8/1992 | MacAluso, Jr. | 604/281 |
| 5,147,370 | 9/1992 | McNamara et al. | 606/108 |
| 5,151,105 | 9/1992 | Kwan-Gett | 623/1 |
| 5,152,784 | 10/1992 | Tsilibary | 623/1 |
| 5,160,341 | 11/1992 | Brenneman et al. | 606/198 |
| 5,167,233 | 12/1992 | Eberle et al. | 600/470 |
| 5,171,273 | 12/1992 | Silver et al. | 623/13 |
| 5,174,302 | 12/1992 | Palmer | 600/585 |
| 5,176,625 | 1/1993 | Brisson | 604/8 |
| 5,176,661 | 1/1993 | Evard et al. | 604/282 |
| 5,183,085 | 2/1993 | Timmermans | 140/89 |
| 5,186,992 | 2/1993 | Kite, III | 428/36.3 |
| 5,197,977 | 3/1993 | Hoffman, Jr. et al. | 623/1 |
| 5,203,772 | 4/1993 | Hammerslag et al. | 604/95 |
| 5,211,183 | 5/1993 | Wilson | 600/585 |
| 5,213,111 | 5/1993 | Cook et al. | 600/585 |
| 5,217,484 | 6/1993 | Marks | 606/200 |
| 5,222,969 | 6/1993 | Gillis | 606/194 |
| 5,226,911 | 7/1993 | Chee et al. | 606/191 |
| 5,228,453 | 7/1993 | Sepetka | 600/585 |
| 5,230,348 | 7/1993 | Ishibe et al. | 600/585 |
| 5,234,456 | 8/1993 | Silvestrini | 606/194 |
| 5,238,004 | 8/1993 | Sahatjian et al. | 600/585 |
| 5,243,996 | 9/1993 | Hall | 600/585 |
| 5,246,014 | 9/1993 | Williams et al. | 607/122 |
| 5,250,071 | 10/1993 | Palermo | 606/198 |
| 5,251,640 | 10/1993 | Osborne | 600/585 |
| 5,256,146 | 10/1993 | Ensminger et al. | 604/104 |
| 5,259,393 | 11/1993 | Corso, Jr. et al. | 600/585 |
| 5,304,194 | 4/1994 | Chee et al. | 606/191 |
| 5,312,415 | 5/1994 | Palermo | 606/108 |
| 5,336,205 | 8/1994 | Zenzen et al. | 604/280 |
| 5,341,818 | 8/1994 | Abrams et al. | 600/585 |
| 5,342,387 | 8/1994 | Summers | 606/198 |
| 5,350,397 | 9/1994 | Palermo et al. | 606/200 |
| 5,354,295 | 10/1994 | Guglielmi et al. | 606/32 |
| 5,368,049 | 11/1994 | Raman et al. | 600/585 |
| 5,373,856 | 12/1994 | Grenouillet | 600/585 |
| 5,382,259 | 1/1995 | Phelps et al. | 606/151 |
| 5,383,887 | 1/1995 | Nadal | 606/200 |
| 5,386,828 | 2/1995 | Owens et al. | 600/585 |
| 5,395,390 | 3/1995 | Simon et al. | 606/198 |
| 5,405,377 | 4/1995 | Cragg | 623/1 |
| 5,409,015 | 4/1995 | Palermo | 600/585 |
| 5,413,597 | 5/1995 | Krajicek | 623/1 |
| 5,415,664 | 5/1995 | Pinchuk | 606/108 |
| 5,423,849 | 6/1995 | Engelson et al. | 606/191 |
| 5,433,723 | 7/1995 | Lindenberg et al. | 606/198 |
| 5,439,485 | 8/1995 | Mar et al. | 607/119 |
| 5,441,516 | 8/1995 | Wang et al. | 606/198 |
| 5,443,478 | 8/1995 | Purdy | 606/200 |
| 5,484,449 | 1/1996 | Amundson et al. | 606/108 |
| 5,500,013 | 3/1996 | Buscemi et al. | 623/1 |
| 5,509,411 | 4/1996 | Littmann et al. | 600/381 |
| 5,514,115 | 5/1996 | Frantzen et al. | 604/281 |
| 5,514,128 | 5/1996 | Hillsman et al. | 606/7 |
| 5,514,176 | 5/1996 | Bosley, Jr. | 623/1 |
| 5,519,172 | 5/1996 | Spencer et al. | 179/110 R |
| 5,520,194 | 5/1996 | Miyata et al. | 600/585 |
| 5,522,836 | 6/1996 | Palermo | 606/200 |
| 5,523,092 | 6/1996 | Hanson et al. | 424/423 |
| 5,540,701 | 7/1996 | Sharkey et al. | 606/153 |
| 5,540,713 | 7/1996 | Schnepp-Pesch et al. | 606/198 |
| 5,549,624 | 8/1996 | Mirigian et al. | 606/191 |
| 5,549,663 | 8/1996 | Cottone, Jr. | 623/1 |
| 5,562,641 | 10/1996 | Flomenblit et al. | 604/281 |
| 5,569,245 | 10/1996 | Guglielmi et al. | 606/49 |
| 5,582,619 | 12/1996 | Ken | 606/191 |
| 5,601,593 | 2/1997 | Freitag | 606/198 |
| 5,603,694 | 2/1997 | Brown et al. | 604/49 |
| 5,607,445 | 3/1997 | Summers | 606/198 |
| 5,609,627 | 3/1997 | Goicoechea et al. | 623/1 |
| 5,613,981 | 3/1997 | Boyle et al. | 606/198 |
| 5,618,301 | 4/1997 | Hauenstein et al. | 606/198 |
| 5,624,461 | 4/1997 | Mariant | 606/191 |
| 5,632,772 | 5/1997 | Alcime et al. | 623/1 |
| 5,637,113 | 6/1997 | Tartaglia et al. | 623/1 |
| 5,639,277 | 6/1997 | Mariant et al. | 606/191 |
| 5,643,254 | 7/1997 | Scheldrup et al. | 606/32 |
| 5,649,949 | 7/1997 | Wallace et al. | 606/191 |
| 5,667,522 | 9/1997 | Flomenblit et al. | 606/198 |
| 5,674,277 | 10/1997 | Freitag | 623/1 |
| 5,676,697 | 10/1997 | McDonald | 623/1 |
| 5,690,643 | 11/1997 | Wijay | 606/108 |
| 5,690,666 | 11/1997 | Berenstein et al. | 606/191 |
| 5,690,671 | 11/1997 | McGurk et al. | 606/200 |
| 5,693,085 | 12/1997 | Buirge et al. | 623/1 |

| | | | | |
|---|---|---|---|---|
| 5,702,373 | | 12/1997 | Samson | 604/282 |
| 5,824,054 | * | 10/1998 | Khosravi et al. | 623/1.44 |
| 5,876,432 | * | 3/1999 | Lau et al. | 606/191 |
| 6,004,346 | * | 12/1999 | Wolff et al. | 623/12 |
| 6,017,362 | * | 1/2000 | Lau | 606/194 |

OTHER PUBLICATIONS

Christos A. Athanasoulis, M.D., The New England Journal of Medicine, May 22, 1980, "Therapeutic Applications of Angiography" pp. 1174–1179 (2 of 2).

Alex Berenstein, M.D. and Irvin I. Kricheff, M.D., "Catheter and Material Selection for Transarterial Embolization: Technical Considerations" Radiology, Sep. 1979; pp. 631–639.

O.A. Battista, et al. Journal of Applied Polymer Science 1967 "Colloidal Macromolecularphenomena. Part II. Novel Microcrystals of Polymers" pp. 481–498.

Sadek K. Hilal, M.D. et al. Journal of Neurological Surgery "Therapeutic Percutaneous Embolization for Extra–Axial Vascular Lesions of the Head, Neck and Spine" Sep., 1975; pp. 275–287.

Stephen L. Kaufman, M.D. et al. Investigative Radiology, May–Jun. 1978, "Transcatheter Embolization with Microfibrillar Collagen in Swine"; pp. 200–204.

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975, "Selective Arterial Embolization for Control of Massive Upper Gastrointestinal Bleeding" pp. 119–126.

Glenn H. Roberson, et al., American Journal of Radiology, Oct. 1979, "Therapeutic Embolization of Juvenile Angiofibroma" pp. 657–663.

Sidney Wallace, M.D. et al., Cancer, Oct. 1979, "Arterial Occulusion of Pelvic Bone Tumors"; pp. 322–325 & 661–663.

"Mechanical Devices for Arterial Occlusion" by C. Gianturco, M.D., et al., Jul. 1975, pp. 428–435.

"Therapeutic Vascular Occlusion Utilizing Steel Coil Technique: Clinical Applications" by Sidney Wallace, et al., Am J. Roentgenol (1976); pp. 381–387.

"Transcatheter Intravascular Coil Occlusion of Experimental Arteriovenous Fistulas", by James H. Anderson, et al., An. J. Roentgenol, Nov. 1977, pp. 795–798.

"'Mini' Gianturco Stainless Steel Coils for Transcatheter Vascular Occlusion" by James H. Anderson, et al., From the Department of Diagnostic Radiology at the University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

* cited by examiner

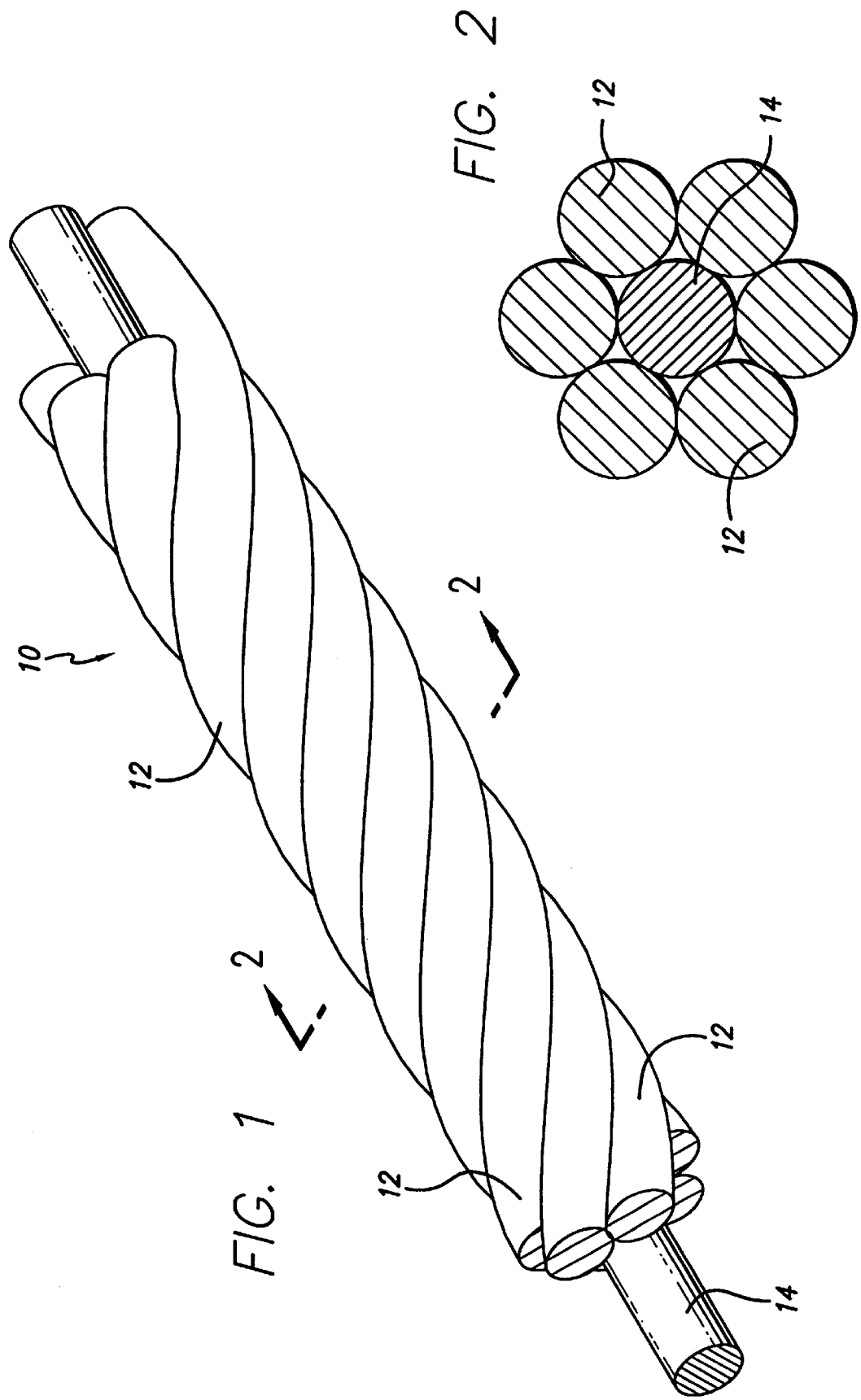

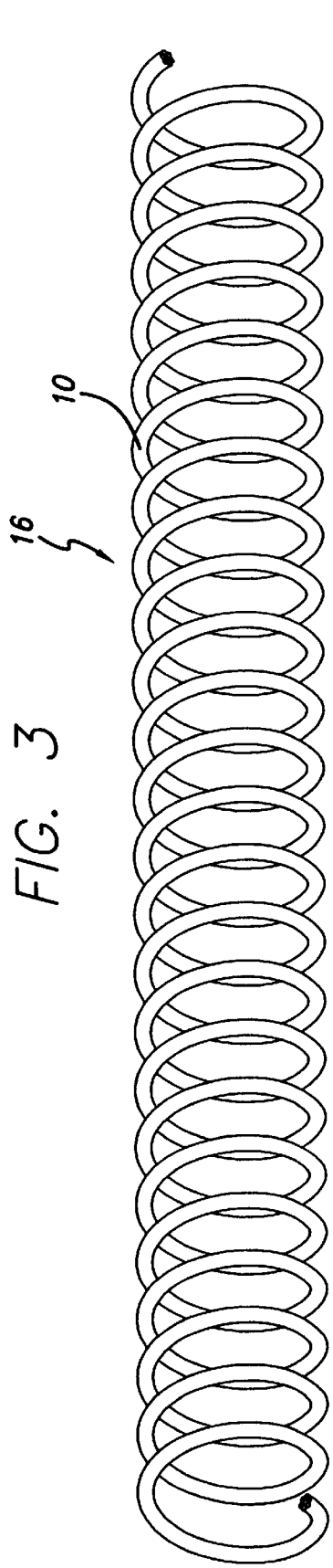
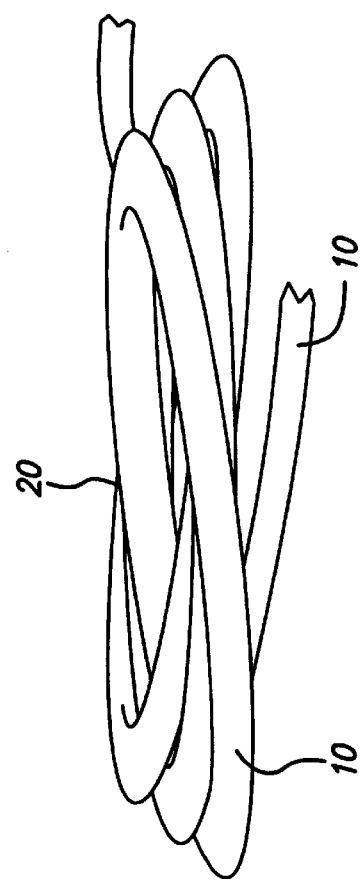
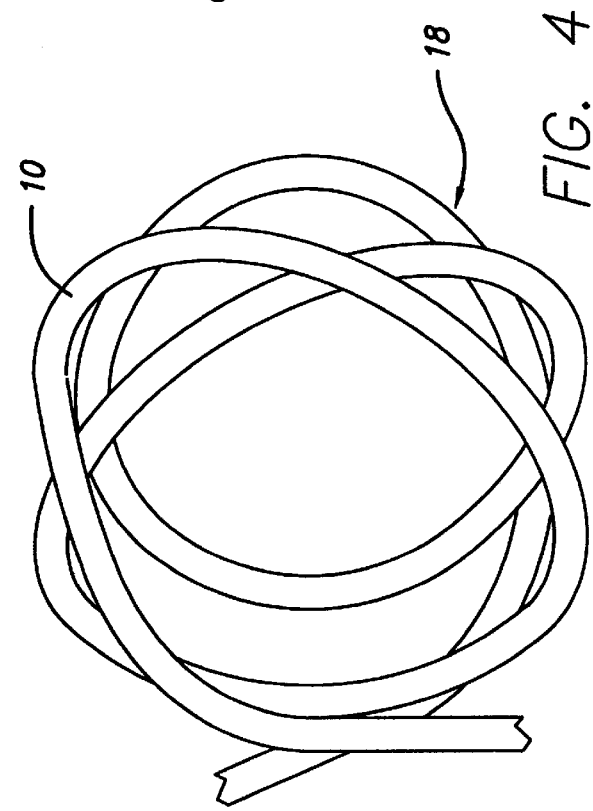
FIG. 3
FIG. 5
FIG. 4

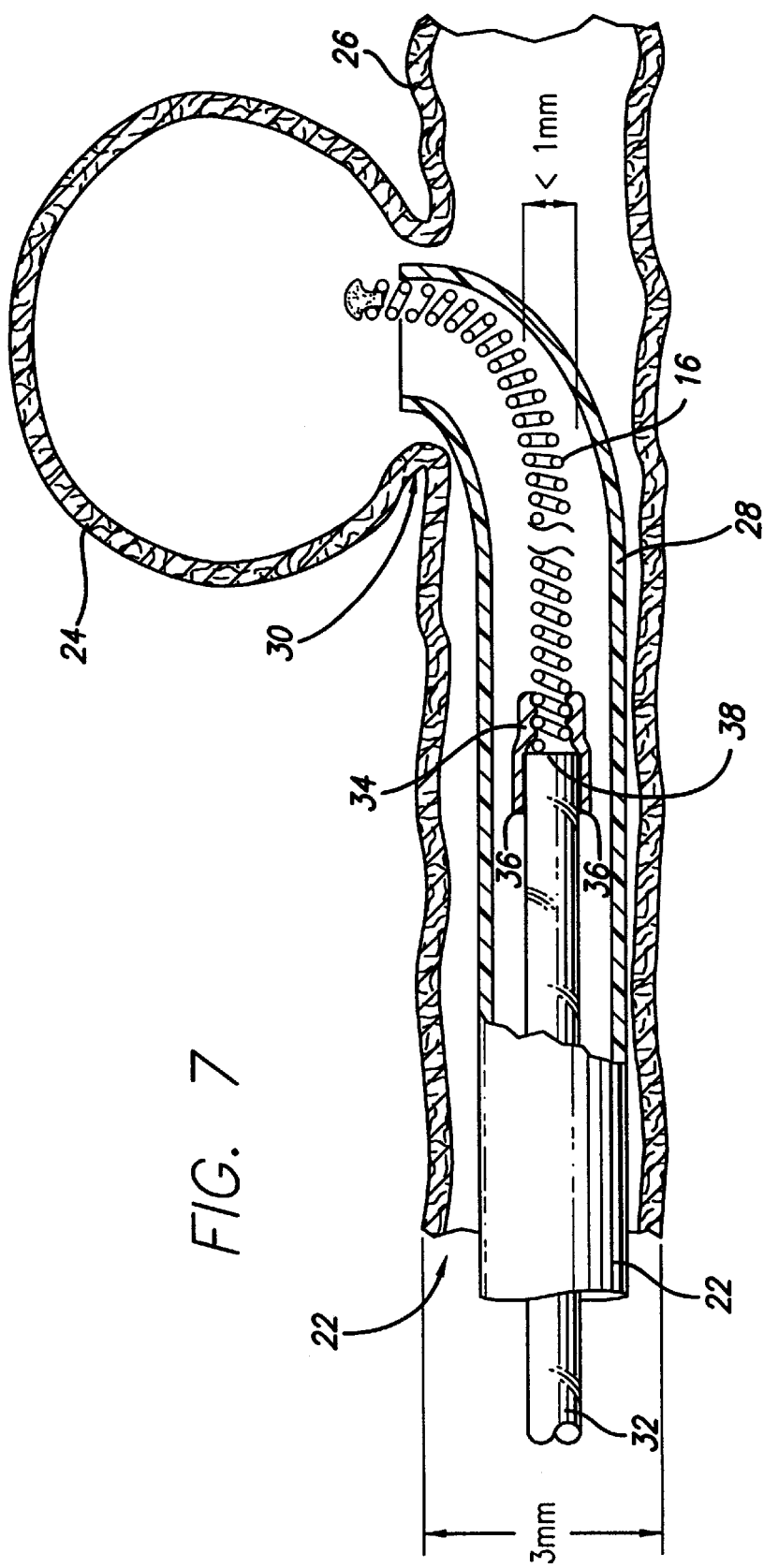

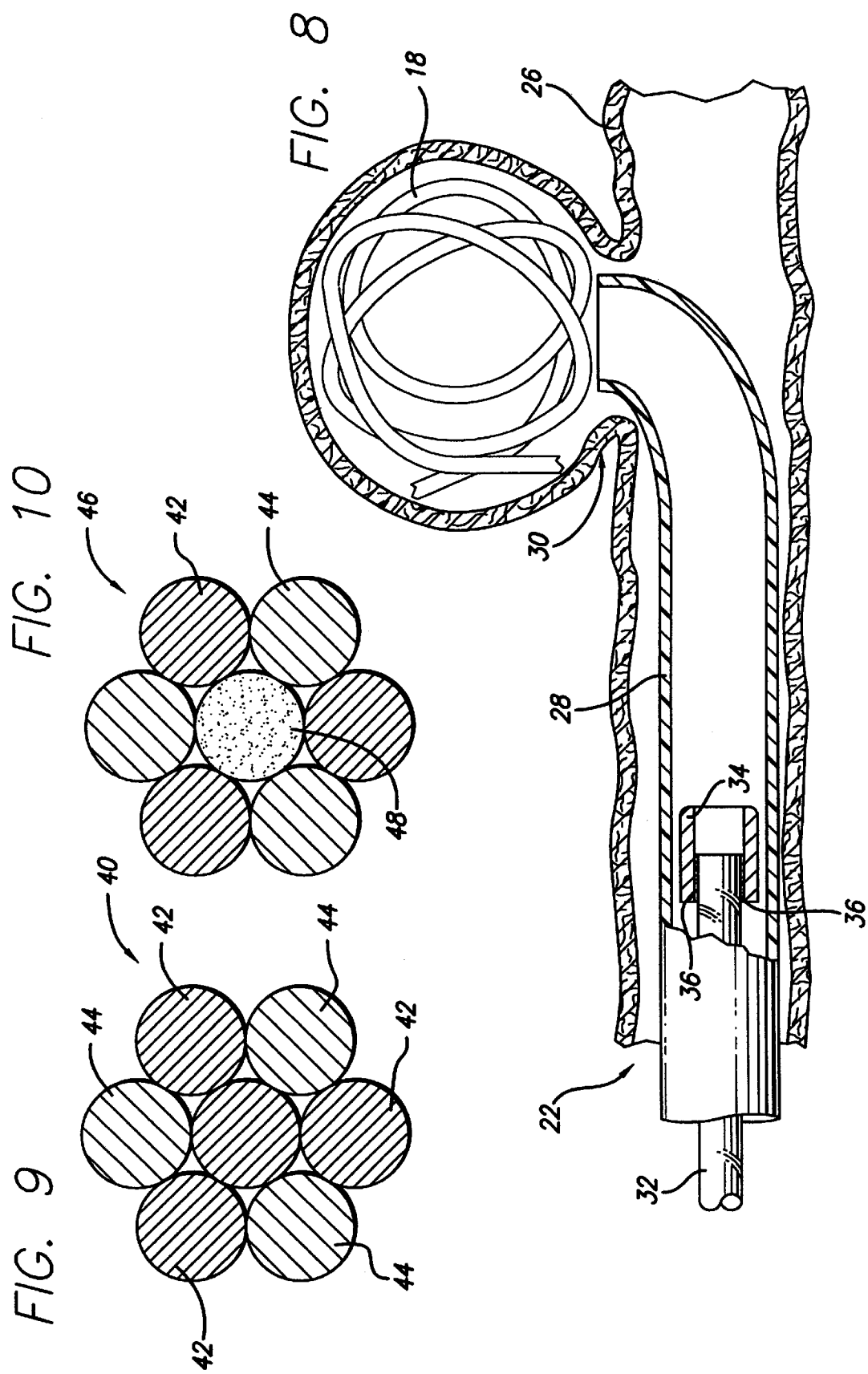

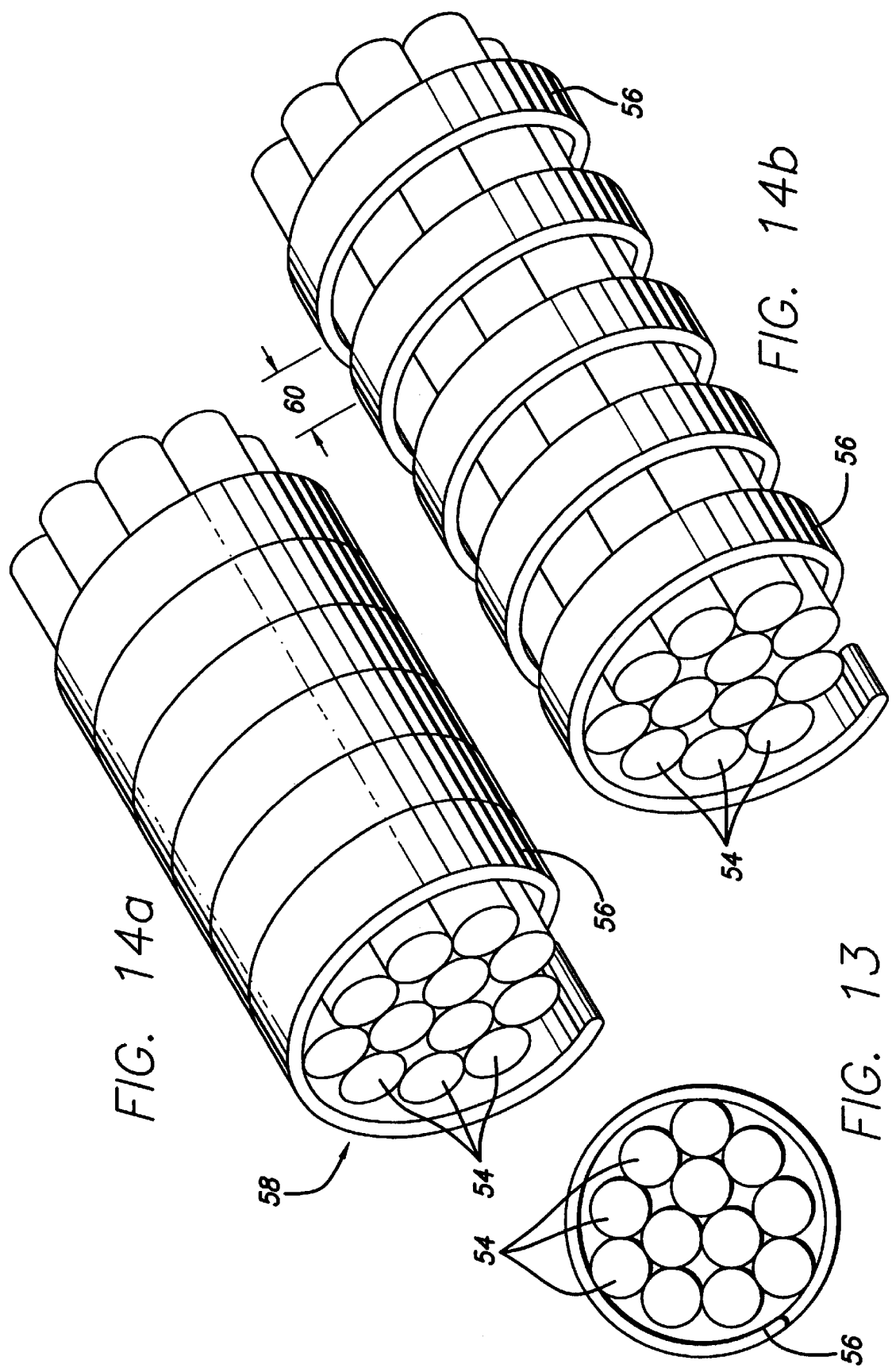

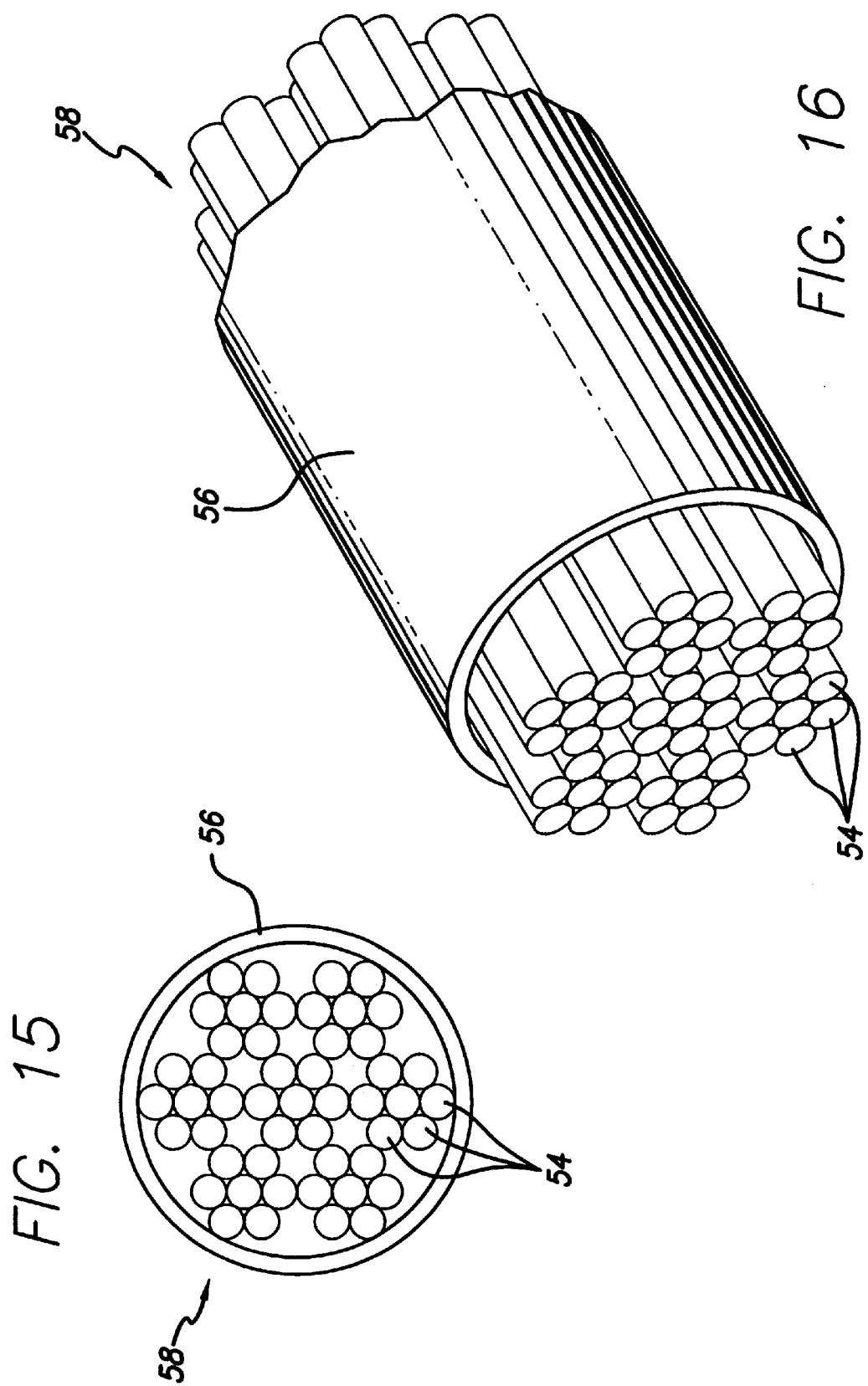

COATED SUPERELASTIC STENT

RELATED APPLICATIONS

This is a continuation of Ser. No. 09/143,507 filed Aug. 28, 1998, now abandoned, which is a continuation in part of Ser. No. 08/986,004 filed Dec. 5, 1997 now abandoned.

BACKGROUND OF THE INVENTION

1. Field of the Invention

This invention relates generally to implantable devices for interventional therapeutic treatment or vascular surgery, and more particularly concerns a coated superelastic stent formed from a stranded micro-cable with enhanced radiopacity.

2. Description of Related Art

The art and science of interventional therapy and surgery has continually progressed towards treatment of internal defects and diseases by use of ever smaller incisions or access through the vasculature or body openings in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like and the use of vasoocclusive devices to treat defects in the vasculature. There is a constant drive by those practicing in the art to develop new and more capable systems for such applications. When coupled with developments in biological treatment capabilities, there is an expanding need for technologies that enhance the performance of interventional therapeutic devices and systems.

One specific field of interventional therapy that has been able to advantageously use recent developments in technology is the treatment of neurovascular defects. More specifically, as smaller and more capable structures and materials have been developed, treatment of vascular defects in the human brain which were previously untreatable or represented unacceptable risks via conventional surgery have become amenable to treatment. One type of nonsurgical therapy that has become advantageous for the treatment of defects in the neurovasculature has been the placement by way of a catheter of vasoocclusive devices in a damaged portion of a vein or artery.

Vasoocclusion devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a preformed strand of flexible material that can be a nickel-titanium alloy is known from U.S. Pat. No. 5,645,558, which is specifically incorporated by reference herein.

The delivery of such vasoocclusive devices can be accomplished by a variety of means, including via a catheter in which the device is pushed through the catheter by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, micro-coils formed of very small diameter wire are used in order to restrict, reinforce, or to occlude such small diameter areas of the vasculature. A variety of materials have been suggested for use in such micro-coils, including nickel-titanium alloys, copper, stainless steel, platinum, tungsten, various plastics or the like, each of which offers certain benefits in various applications. Nickel-titanium alloys are particularly advantageous for the fabrication of such micro coils, in that they can have super-elastic or shape memory properties, and thus can be manufactured to easily fit into a linear portion of a catheter, but attain their originally formed, more complex shape when deployed. Although various materials are more or less kink resistant when nickel-titanium alloys are dimensioned into wire smaller than approximately 0.010 inches in diameter, they can have low yield strength and can kink more easily, thus severely limiting the applications for such finely drawn wire in the fabrication of vasoocclusive devices. As a further limitation to such applications, nickel-titanium alloys are also not radiopaque in small diameters, and a single nickel-titanium wire would need to be approximately 0.012 inches in diameter to be even slightly radiopaque. However, such a thickness of a single nickel-titanium wire would unfortunately also be relatively stiff and possibly traumatic to the placement site, particularly if used for treatment of delicate and already damaged areas of the small diameter vasculature such as an aneurysm in an artery or vein in the brain, for example.

One conventional guidewire for use in a catheter is known that is made of a high elasticity nickel-titanium alloy, and is useful for accessing peripheral or soft tissue targets. The distal tip of the guidewire is provided with a radiopaque flexible coil tip, and a radiopaque end cap is attached to the guidewire by a radiopaque ribbon. Such a construction is complex to manufacture, fragile and can potentially break off during use with undesirable results. A stretch resistant vasoocclusive coil is also known that can be made of a primary helically wound coil of platinum wire, with a stretch-resisting wire attached within the primary coil between two end caps. Unfortunately, such a construction is relatively difficult to fabricate and also fragile, allowing for the possibility of the fracture of the central radiopaque wire, the coil, the welds or some combination of them, and it can also potentially break off during use. Also, such a construction has a complex and nonlinear bending characteristic, dependent on the spacing of the coils and central wire and the radius of the bend of the coil.

Stents are typically implanted within a vessel in a contracted state and expanded when in place in the vessel in order to maintain patency of the vessel, and such stents are typically implanted by mounting the stent on a balloon portion of a balloon catheter, positioning the stent in a body lumen, and expanding the stent to an expanded state by inflating the balloon. The balloon is then deflated and removed, leaving the stent in place. However, the placement, inflation and deflation of a balloon catheter is a complicated procedure that involves additional risks beyond the implantation of the stent, so that it would be desirable to provide a stent that can be more simply placed in the site to be treated in a compressed state, and expanded to leave the stent in place.

Stents also commonly have a metallic structure to provide the strength required to function as a stent, but typically do not provide for the delivery of localized therapeutic pharmacological treatment of a vessel at the location being treated with the stent. Stents formed of polymeric materials capable of absorbing and releasing therapeutic agents may not provide adequate structural and mechanical requirements for a stent, especially when the polymeric materials are loaded with a drug, since drug loading of a polymeric material can significantly affect the structural and mechanical properties of the polymeric material. Since it is frequently desirable to be able to provide localized therapeutic pharmacological treatment of a vessel at the location being treated with the stent, it would be desirable to combine such polymeric materials with a stent structure to provide the stent with the capability of absorbing and delivering therapeutic drugs or other agents at a specific site in the vasculature to be treated.

Conventional forms of stents are known that have a covering or outer layers of collagen, that can be used for enhancing biocompatability and for drug delivery. One known tubular metal stent, for example, is combined with a covering sleeve of collagen in order to increase the biocompatibility of the stent upon implantation. The collagen sleeve may be collagen per se or a collagen carried on a support of Dacron or a similar material. Another three-layer type of vascular prosthesis has two outer layers formed of collagen, and a middle layer made from inert fibers such as synthetic fibers. Another tubular reinforcing structure for use as a cardiovascular graft is made of collagenous tissue with a reinforcing fibrous structure surrounding the lumen. One drug delivery collagen-impregnated synthetic vascular graft is also known, formed from a porous synthetic material having collagen such that the graft substrate cross-links the collagen in order to render the substrate blood-tight. A matrix is also provided in another biodegradable drug delivery vascular stent that is made from collagen or other connective proteins or natural materials that can be saturated with drugs. However, none of these types of stents provide for a coated, superelastic shape memory stent that can be delivered and released at the site in the vasculature to be treated in a compressed state, and expanded to leave the stent in place without the need for placement with a balloon catheter.

From the above, it can be seen that vasoocclusive devices and stents provide important improvements in the treatment of the vasculature. However, it would be desirable to provide a structural element that used to form a coated stent, that offers the advantages of a shape memory alloy such as a nickel-titanium alloy, and that incorporates radiopaque material in a stable configuration that is not subject to breaking during use of the device, so that the device can be visualized under fluoroscopy. The present invention meets these and other needs.

SUMMARY OF THE INVENTION

Significant advances have been made in the treatment of neurovascular defects without resolution to surgery. More specifically, micro catheters have been developed which allow the placement of vasoocclusive devices in an area of the vasculature which has been damaged. In presently used techniques, the vasoocclusive devices take the form of spiral wound wires that can take more complex three dimensional shapes as they are inserted into the area to be treated. By using materials that are highly flexible, or even super-elastic and relatively small in diameter, the wires can be installed in a micro-catheter in a relatively linear configuration and assume a more complex shape as it is forced from the distal end of the catheter.

In order to gain the advantages presently being realized with microcatheter therapies and procedures to repair damage to the vasculature in the brain and other vessels, shape memory materials such as nickel-titanium alloys have been incorporated in vasoocclusive devices to be placed by the catheters. However, the range of diameters ofwire and the configurations of the resulting geometry of both the coils and the devices developed which can be used have been limited by both the relatively small diameter of wire that must be used to avoid trauma and allow housing within the catheter prior to deployment, and the requirement for larger diameters to provide for radiopaque markers and mechanical robustness. In many cases this has resulted in primary wire characteristics in the coil that are unacceptably stiff, very delicate, or subject to kinking. The present invention obtains significant advantages over such prior art devices by providing a cable of multiple strands of an alloy adapted to be used in catheters, stents, vasoocclusive devices, guidewires and the like, thus providing a kink resistant, high strength material with highly desirable performance characteristics which can be altered by construction details to suit a variety of interventional therapeutic procedures.

More specifically, it has been found that single strands of small diameter nickel-titanium alloys, as well as other metal alloys, used to form vasoocclusive devices can be kinked if twisted and pulled as can occur during or after deployment from a catheter, especially if the doctor wishes to withdraw a partially deployed coil because it is somehow incorrect in size, shape or length to repair the damage to the vessel. Also, single wire coils are more likely to cause trauma to the area to be treated if the wire is of a sufficient diameter to provide adequate tensile strength. Furthermore, such small diameter wires of some of these materials such as nickel-titanium, stainless steel and the like, are not generally radiopaque with currently available equipment, necessitating the use of radiopaque markers attached to the device, with the resultant possible diminution of functionality and increased diameter.

The present invention solves these and other problems by providing, in its broadest aspect, a superelastic collagen coated stent formed from a micro-cable which includes at least one radiopaque strand to offer a continuous indication under fluoroscopy of the deployed configuration of the device incorporating the micro-cable. When combined with the benefits of a material such as nickel-titanium in the other strands of the micro-cable, numerous advantages are available from the use of this basic construction in interventional medicine. The shape of the superelastic collagen coated stent can contour to the shape of the anatomical cavity or portion of the vasculature, and the superelastic collagen coated stent would provide an adequate surface area of collagen for contact with a vessel wall to deliver drugs to the vessel wall.

Briefly, and in general terms, a presently preferred embodiment of the present invention provides for a superelastic collagen coated stent formed from a multistranded micro-cable made of a suitable material such as stainless steel or a nickel-titanium alloy, with the cable including at least one radiopaque strand, made of platinum, tungsten or gold, in order to serve as a marker during a procedure. The multi-stranded micro-cable can be configured into a stent to reinforce areas of the small diameter vasculature such as an artery or vein in the brain, for example. The superelastic collagen coated stent can be formed as a helical ribbon or tape, supported internally by a superelastic structure that can be compressed along the width and length of the stent structure, to be pushed by a pusher member through a microcatheter or cannula. When deployed in a helical configuration, with a ribbon cross-section, a closed helical pitch is achieved, providing a collagen tube in contact with the vessel wall. The stent is detachable from the pusher member. The superelastic collagen coated stent can be manufactured by producing the superelastic inner structure, compressing the structure, sliding it into a collagen tube, and allowing the superelastic inner structure to expand and flatten the tube into a ribbon. The collagen tube of the superelastic collagen coated stent is preferably loaded with a therapeutic agent or drug to reduce or prevent restenosis and thrombosis in the vessel being treated.

In one presently preferred embodiment, the invention accordingly provides for a superelastic collagen coated stent formed from a multi-stranded micro-cable having a plurality of flexible strands of a super elastic material, and at least one radiopaque strand. In one presently preferred embodiment, the multi-stranded micro-cable comprises a plurality of flexible strands of nickel-titanium alloy, the micro-cable having at least one central axially disposed radiopaque wire, such as platinum, tungsten or gold, for example, in order to provide a radiopaque marker during vascular procedures. In this preferred embodiment, the construction of the invention places the lowest tensile strength and highest flexibility member, the radiopaque marker strand, in a position in the cable which results in minimum stress on that member; at the same time, the superelastic material is in the outer strands, which have the dominant affect on performance parameters, thus enhancing the benefits of the material. Another benefit associated with the invention compared to prior art devices is that the multiple stranded cable configuration, in addition to providing a highly flexible and resilient structure, eliminates the necessity of a safety wire, since the failure of a single strand will not cause a severing of the cable. Also, the construction prevents stretching of the cable in the event of failure of a single strand, which is a significant benefit compared to constructions which have a coil around a central safety wire.

In a second presently preferred embodiment, the invention includes a superelastic collagen coated stent formed from a multi stranded cable constructed of multiple twisted strands of a suitable material such as a shape memory alloy or super elastic alloy of nickel-titanium, with one or more of the twisted strands consisting of a radiopaque material. The radiopaque strand may be one or more of the peripheral twisted strands and may also include one or more central strands of the cable. In a preferred aspect of the embodiment, the cable consists of six peripheral twisted strands and a central linear core strand, one or more of which can be of radiopaque material.

In a third aspect of the invention, the cable forming the superelastic collagen coated stent can be of linear strands that are arranged in a bundle and fastened or bound at intervals, or continuously, in order to maintain contact among the strands as the cable is bent. One or more of the strands may be radiopaque. This construction is adaptable to guidewires and other structures that must be pushable and/or torqueable, but still remain highly flexible and include radiopacity. Variations on this embodiment can include an outer sheath which consists of a solid or helically wound cover to provide enhanced torqueability and pushability. More specifically, the outer sheath can vary in thickness, stiffness of material or spring of the sheath members to provide desired variations in bending or stiffness of the cable. Such a construction is particularly adaptable to guidewires and the like, and can be varied in terms of the binding or outer layer to alter the torqueability of the cable, and the flexibility of the cable can be varied along its length by the number and sizes of the stranded members in the cable.

In a fourth aspect of the invention, one or more of the strands of the superelastic collagen coated stent can be of a therapeutic material used to enhance treatment of the site after placement of the device. In one presently preferred embodiment of the invention, the cable includes twisted strands of wire around the periphery of the cable, at least one of which is radiopaque. The core of the cable contains a therapeutic agent such as human growth hormone, genetic material, antigens or the like that are intended to become active after placement. Such a construction can be adapted to a variety of interventional therapeutic treatments. In one aspect of this embodiment, one of the strands can have multiple functions, such as providing both a therapeutic effect and also contributing to the structural integrity of the cable. By using copper in such a micro-cable, for instance, the copper can enhance the use of a device made from the cable as on intra-uterine device, with the copper also contributing to the radiopacity and structural integrity of the micro-cable. In the event that such an effect is desired, the therapeutic strand can be placed on the exterior of the cable to enhance contact with the site to be treated.

These and other aspects and advantages of the invention will become apparent from the following detailed description and the accompanying drawing, which illustrates by way of example the features of the invention.

BRIEF DESCRIPTION OF THE DRAWINGS

FIG. 1 is a perspective of a radiopaque microstrand cable according to the invention.

FIG. 2 is a cross-section at 2—2 of FIG. 1.

FIG. 3 is a helical vasoocclusive coil formed of the cable of the invention.

FIG. 4 is a spherical vasoocclusive structure formed using the cable of the invention.

FIG. 5 is a stacked coil vasoocclusive device formed using the cable of the invention.

FIG. 7 is an illustration of a vasoocclusive coil which has been introduced into an aneurysm preparatory to being deployed within the aneurysm.

FIG. 8 is an illustration of a spherical vasoocclusive coil formed with cable of the invention deployed within an aneurysm.

FIG. 9 is an alternate preferred embodiment of the invention including a plurality of radiopaque strands within the cable.

FIG. 10 is an alternate preferred embodiment incorporating a therapeutic member within the radiopaque cable of the invention.

FIG. 13 is an alternative embodiment to the embodiment of FIG. 12 wherein the external binding of the cable represents a sheath wound about the cable.

FIGS. 14a and 14b are perspectives of alternative embodiments of the embodiment of FIG. 13.

FIG. 15 is a cross-section of an alternative embodiment in which a plurality of multi-strand cables are included within an external sheath surrounding the cable.

FIG. 16 is a perspective view of the embodiment of FIG. 15.

DETAILED DESCRIPTION OF THE PREFERRED EMBODIMENTS

Figure 6:
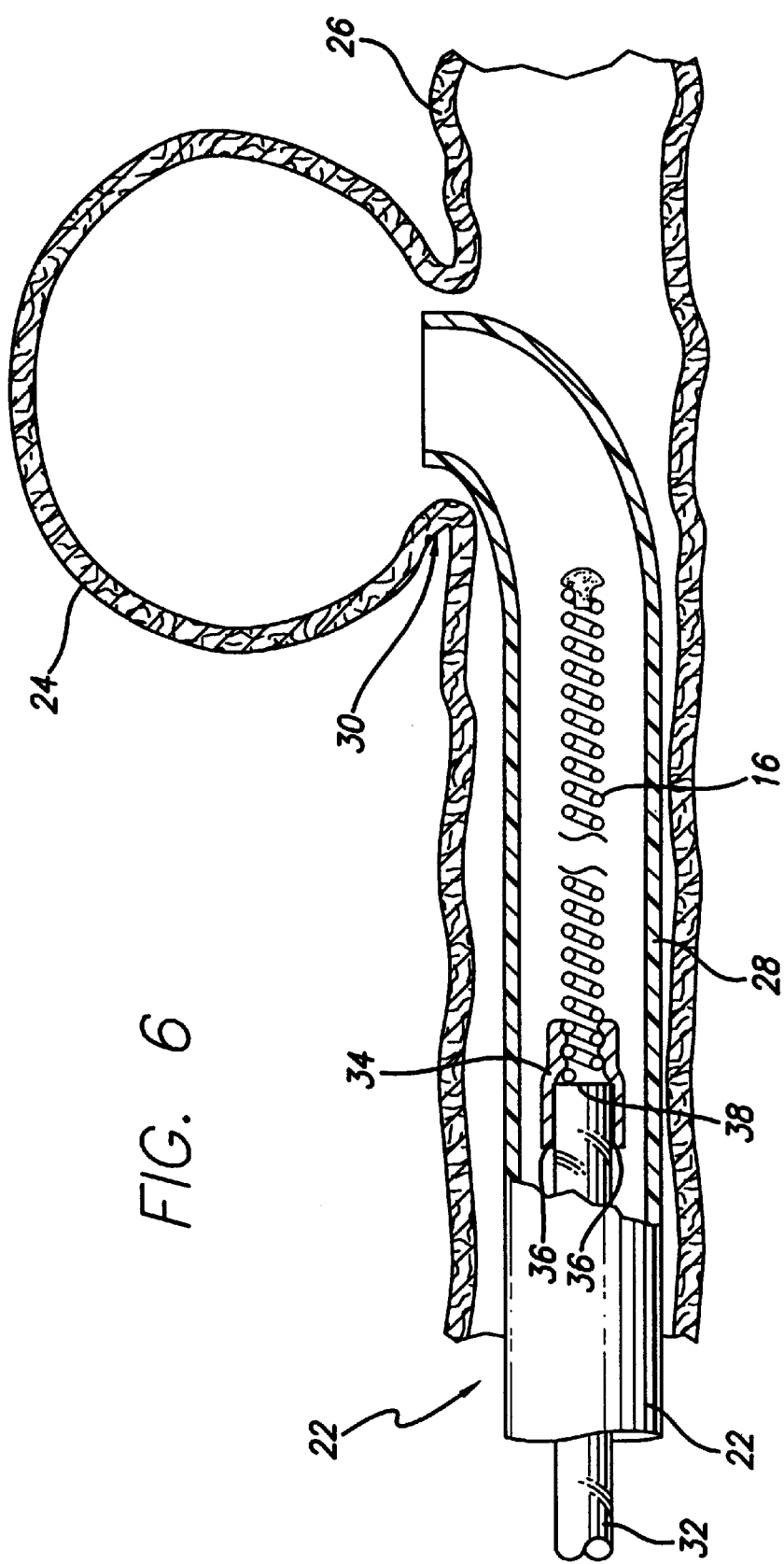
FIG. 6 is a cross section of a vascular member with an aneurysm illustrating the approach of a vasoocclusive coil towards the aneurysm.

While nickel-titanium alloys are useful in forming superelastic or shape memory interventional devices, micro-coils formed of very small diameter wires of nickel-titanium alloy material for treatment of areas of the small diameter vasculature such as an artery or vein in the brain, for treatment of aneurysms and the like, for example, can have relatively low yield strengths and are somewhat subject to kinking, even if made of super-elastic alloy. This can create problems if the coil is to be withdrawn after being emplaced by the doctor, as for instance, if the device is too small to effectively fill the cavity to be treated. Furthermore, even solid wires of a size suitable for use in interventional devices are not very radiopaque.

While stents can be implanted within a vessel in a contracted state and expanded when in place in the vessel in order to maintain patency of the vessel, and typically have a metallic structure to provide the strength required to function as a stent, metallic stents typically do not provide for the delivery of localized therapeutic pharmacological treatment of a vessel at the location being treated with the stent, and typically can not be delivered and released at the site in the vasculature to be treated in a compressed state, and expanded to leave the stent in place without the need for placement of the stent with a balloon catheter.

As is illustrated in the drawings, which are provided for the purposes of illustration and not by way of limitation, the invention is embodied in a multi-stranded micro-cable formed of a plurality of flexible strands of a resilient material with the cable including at least one radiopaque strand. In a presently preferred embodiment of the invention illustrated in FIG. 1, the multi-stranded micro-cable 10 is approximately from 0.0021 to 0.0045 inches in diameter, and comprises a plurality of flexible strands 12 of nickel-titanium alloy, with at least one centrally, axially disposed radiopaque wire 14 which is approximately from 0.0007 to 0.0015 inches in diameter. While the above stated diameters represent those presently known to be compatible with the invention, larger or smaller diameters may be useful for particular applications. The central radiopaque wire 14 can be formed of platinum or gold, for example, or other similar suitable radiopaque metals, in order to provide a radiopaque marker of the deployed configuration of a device made of the cable during vascular surgery.

There are numerous benefits to the novel construction of the invention for use in interventional devices and the like. By using the stranded or micro-cable construction of the invention, a device made from the micro-cable becomes virtually kink resistant compared to the single strand wires now commonly used in micro-coils. The multi-strand cable construction of the invention allows the micro-wires of the cable to slip across each other and reinforce each other rather than break or take a set. Also, by incorporating a stranded radiopaque material such as platinum, tungsten or gold into the cable construction, the device is radiopaque in sizes much smaller than with other constructions. The micro-cable construction of the invention can be used to produce soft, kink resistant, radiopaque stents, guidewires, guidewire distal tips, and microcoils.

FIG. 2 is a cross-section of the micro-cable of FIG. 1 at 2—2 illustrating one presently preferred arrangement of the strands within the cable. In this embodiment, the exterior strands 12 are formed of a resilient material chosen to provide the characteristics desired for a specific application in interventional therapies. In a presently preferred embodiment, this material is a nickel titanium super-elastic alloy which is heat treated such that the alloy is highly flexible at a temperature appropriate for introduction into the body via a catheter. By choosing such a material for micro-coils and the like, the devices formed from the micro-cable can be relatively easily placed into the appropriate body cavity and after placement, the device will take on a shape designed to optimize the therapeutic purposes desired for the device. As illustrated in FIG. 2, such a cable can have a central core 14 of a radiopaque material such as gold or platinum, thus dramatically enhancing the radiopacity of the cable. Even a solid super-elastic wire of the same diameter as the cable would have substantially less radiopacity than the cable of the invention with the central gold or platinum wire and the construction of the invention provides numerous other highly desirable characteristics. Among these characteristics is the relative flexibility and resistance to kinking of the cable compared to an equivalent single wire and substantially greater accommodation of the cable to bending, etc., with resultant lessening of trauma to the surrounding tissue and ease of placement in a small body cavity.

One advantageous application of the invention is to vasoocclusive devices formed of the micro-cable for insertion into aneurysms and other vascular defects for the purpose of occluding flow to the aneurysm. FIG. 3 illustrates a helically wound coil 16 of micro-cable 10 which is formed to fit within a micro-catheter for insertion into an area upon which a therapeutic procedure is to be performed. While a helical coil is illustrated, it will be appreciated that numerous other secondary shapes can be formed from the cable of the invention. More specifically, as illustrated in FIG. 4, a three dimensional, essentially spherical, device 18 can be formed of the cable 10, (or even of a coil of the cable, if appropriate) at a temperature sufficient to heat treat the material and thereby create a memory of the desired shape. The device is then inserted into a catheter from which it may be deployed into an aneurysm or the like. The teachings of U.S. Pat. No. 5,645,558 describe the construction of such a device out of flexible wire and are incorporated by referenced herein. FIG. 5 illustrates a collapsed coil configuration 20 for a vasoocclusive device which also can be formed from the cable of the invention and is used for the purposes of insertion into aneurysms and other defects that have relatively large entry necks compared to their internal volume.

FIG. 6 is an illustration of a catheter 22 using a coil 16 as a vasoocclusive device made of the present invention and used for insertion into an aneurysm 24 projecting laterally from a blood vessel 26. The coil 16 is contained within the outer housing 28 of a micro-catheter that is used to house the coil prior to deployment. The end of the catheter housing 28 is introduced into the opening 30 of the aneurism 24 by use of a guide wire (note shown). Thereafter, the vasoocclusive coil 16, and a pusher 32 are introduced into the catheter to provide for insertion of the vasoocclusive device into the aneurysm. In a presently preferred embodiment, the coil 16 formed of the cable of the invention is retained to an optical fiber pusher 32 which is attached to the coil by a collar of shape memory plastic material 34 as described in co-pending application Ser. Nos. 09/019,841 and 09/072,314 the disclosure of which are incorporated herein by reference. As shown in FIG. 7, the coil is introduced into the aneurysm and is then pushed from the micro-catheter until it fills the cavity.

Those skilled in the art will recognize that it is sometimes the case that the vasoocclusive device must be withdrawn after it is fully or partly inserted into the aneurysm. In such a case, there is a danger that the coil will be stretched beyond its elastic range or kink, or otherwise deform and make withdrawal difficult. Those skilled in the art will also recognize that it is sometimes advantageous to form vasoocclusive devices of secondary shapes which are based upon a basic configuration of a coil or the like. The present invention includes such applications within the scope of the invention. However, when vasoocclusive devices made of even super-elastic material are used, it is sometimes the case that the devices will be stretched or kinked when withdrawal is attempted. The cable of the present invention substantially reduces the probability that kinking or stretching beyond yield will occur in a given instance, while at the same time providing radiopacity not available with other constructions. Thus, the present invention represents an important forward step in the technology of interventional therapy.

In one presently preferred embodiment, the shape memory collar 34 is heated to a temperature which allows it to be shrunk onto coil 16. The collar is attached to optical fiber pusher 32 by an adhesive 36 which retains high strength at temperatures beyond the shape memory material transition point. After insertion, and when the operator is satisfied that the device is properly deployed, light energy from a source of coherent light is introduced into the proximal end of the optimal fiber (not shown) and propagated in the distal end 38 of the fiber to cause the shape memory material collar 34 to return to its previous shape and release coil 16. Those skilled in the art will recognize that the invention can also be used with a variety of other placement catheter systems, and it is not intended that the invention be limited to the placement concepts illustrated by way of example.

Those skilled in the art will recognize that a number of shaped devices may be introduced into an area to be treated depending upon its geometry and the number of devices to be inserted. FIG. 8 illustrates an essentially spherical device 18 which has been deployed into such an aneurysm but it will commonly be found that a device such as that shown would then be supplemented by a further coiled device inserted within the space inside the spherical device to completely occlude flow from the artery to the aneurysm.

While one presently preferred implementation of the micro-cable of the invention has been illustrated, those skilled in the art will appreciate that other variations of the invention may have advantages for certain purposes. FIG. 9 is an example of one such construction 40 in which radiopacity is more desirable than in other forms and for that reason a number of radiopaque strands 42, in this illustration four in number, are formed into the cable along with three resilient material strands 44. It will also be appreciated that a larger or smaller number of strands may be incorporated into a given cable and the cables may be formed of multiple cables in order to provide desired bending and strength characteristics. It will also be appreciated by those skilled in the art that the invention is adaptable to the use of a variety of materials which by themselves would not have been easily adaptable to micro devices for interventional therapies. For instance, materials such as copper are useful for intrauterine devices and the like, but copper wire, even when heavily alloyed, has certain limitations for use in such devices. By use of the present invention, composite cables incorporating one or more strands of a desired material can be configured with other strands providing strength, flexibility, shape memory, super-elasticity, radiopacity or the like for previously unavailable characteristics in micro devices.

The invention is also adaptable to numerous other purposes. FIG. 10 illustrates a cross-section of a further preferred embodiment in which radiopaque strands 42 and resilient strands 44 form a portion of the cable 46 and a therapeutic agent 48 is contained in one of the strands. Such a therapeutic agent can include human growth hormone, hydrogels, or a variety of other agents which will serve to provide desired therapeutic capabilities when placed within a specific area of the body being treated by use of the micro-catheter. Depending upon the application of the therapeutic agent, its method of action and the delay, if any, in the time after placement in which the therapeutic action is desired, the agent strand may be placed in any of a variety of positions with the cable, from core wire outward. Also, it may be desirable to coat one or more strands with a therapeutic material for certain purposes. Such constructions are contemplated within the scope of the invention.

Figure 12:
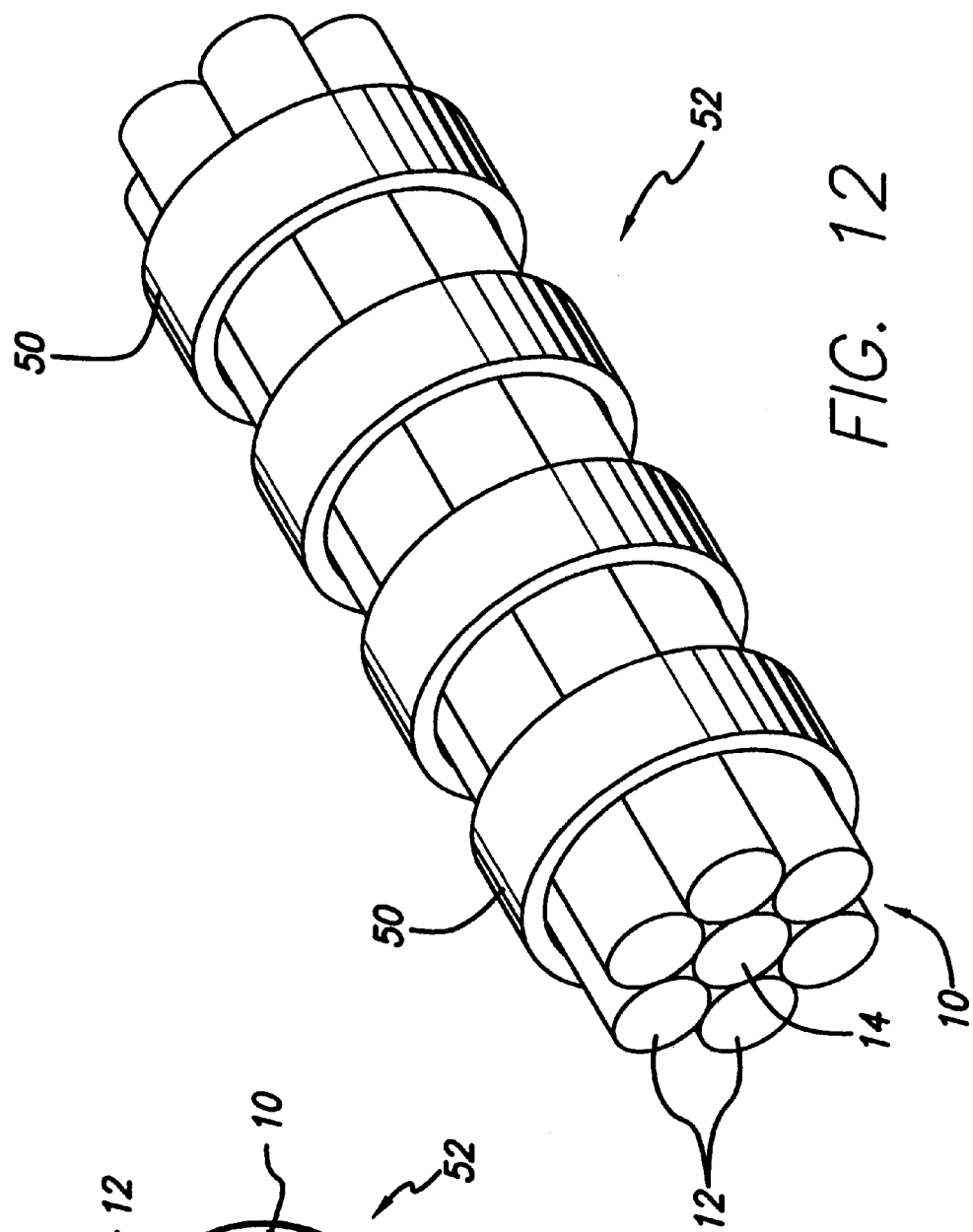
FIG. 12 is a perspective view of the embodiment of FIG. 11.
Figure 11:
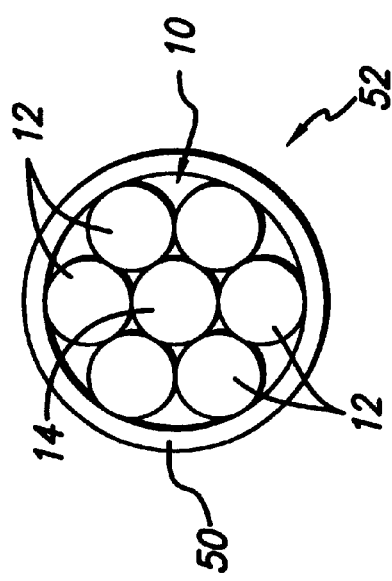
FIG. 11 is an alternate preferred embodiment of the present invention wherein strands of the cable are arranged within an exterior binding consisting of multiple straps about the cable.
Figures 17, 18A, 18B:
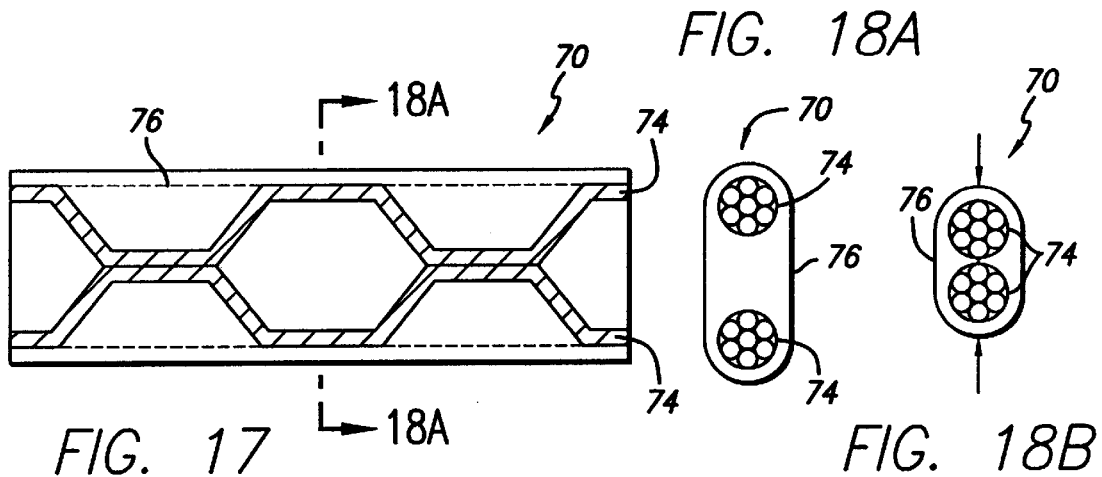
FIG. 17 is a longitudinal sectional partial view of a flattened ribbon of a first embodiment of the superelastic collagen coated stent according to the principles of the invention.
FIG. 18A is a transverse sectional view of the flattened ribbon of the superelastic collagen coated stent taken along line 18—18 of FIG. 17.
FIG. 18B is a transverse sectional view showing the compressed width of the flattened ribbon of the superelastic collagen coated stent of FIG. 18A.
Figures 19, 20A, 20B:
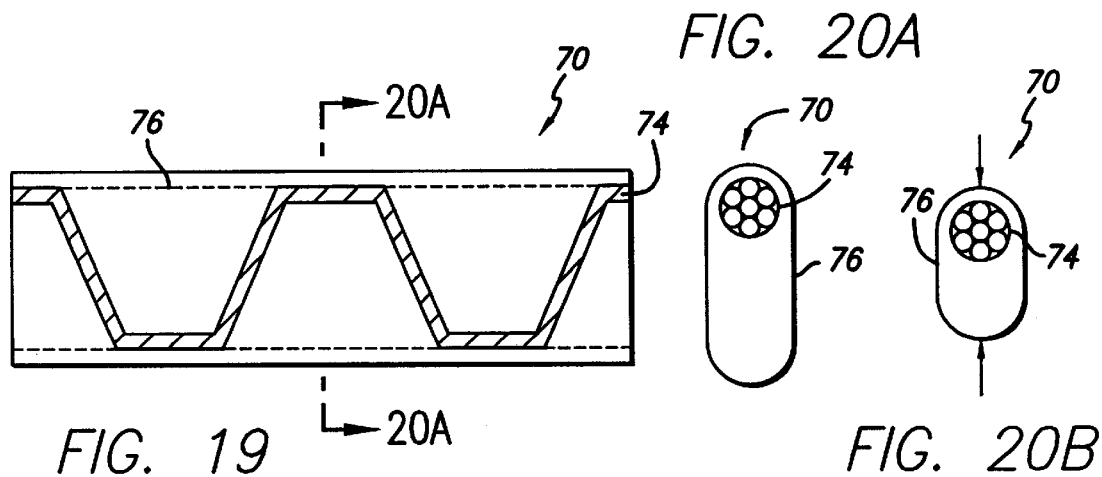
FIG. 19 is a longitudinal sectional partial view of a flattened ribbon of a second embodiment of the superelastic collagen coated stent according to the principles of the invention.
FIG. 20A is a transverse sectional view of the flattened ribbon of the superelastic collagen coated stent taken along line 20—20 of FIG. 19.
FIG. 20B is a transverse sectional view showing the compressed width of the flattened ribbon of the superelastic collagen coated stent of FIG. 20A.
Figures 21, 22A, 22B:
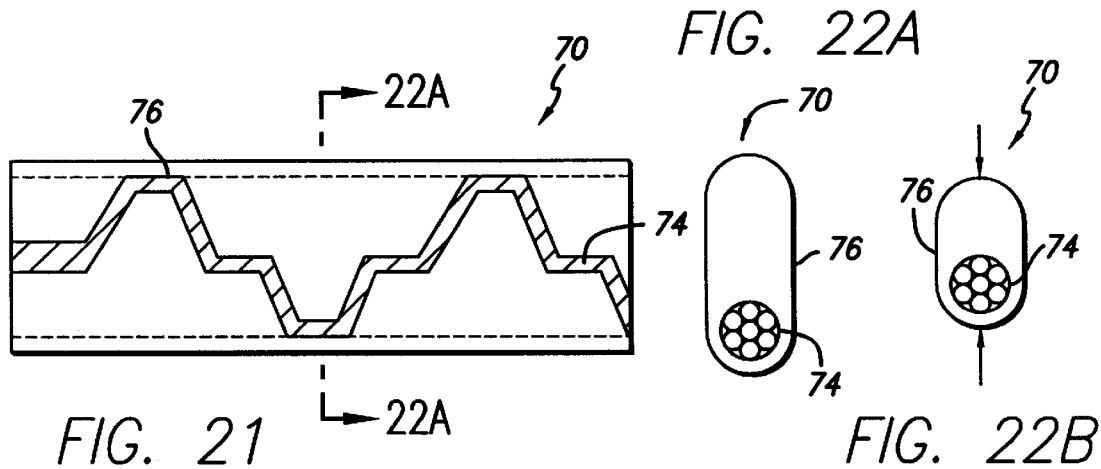
FIG. 21 is a longitudinal sectional partial view of a flattened ribbon of a third embodiment of the superelastic collagen coated stent according to the principles of the invention.
FIG. 22A is a transverse sectional view of the flattened ribbon of the superelastic collagen coated stent taken along line 22—22 of FIG. 21.
FIG. 22B is a transverse sectional view showing the compressed width of the flattened ribbon of the superelastic collagen coated stent of FIG. 22A.

FIG. 11 illustrates a cross-section of an additional presently preferred embodiment of the invention in which the strands 12, 14 of the micro-cable 10 are bundled and banded at intervals by bands 50 to produce a composite banded cable 52 in order to provide increased flexibility without unraveling or dislocation of the strands in the cable. FIG. 12 is a perspective view of the banded cable 50 of this embodiment. While the illustrated configuration shows the strands being laid parallel within the cable, it is also possible in this construction to include both twisted cables as the primary cables 10 within the outer bands 50 to form the composite cable 52. This configuration can use one or more longitudinal strands 14 which are radiopaque, thus providing a continuous indication of radiopacity within the cable. As a further alternative embodiment, it is possible for the longitudinal cable 52 to be formed of a single inner cable 10 with bands 50.

FIG. 13 illustrates a further embodiment of the invention in which longitudinal strands of cables 54 are contained within a wound cover 56 for the purposes of providing a composite guide wire or the like 58 having improved torqueability. Such a construction has particular advantages for guidewire designs having improved radiopacity in very small diameters. It will be appreciated that in this configuration, as well as the other longitudinally arranged multi-stranded cables, the number of strands and the degree to which they extend along the cable within the sheath is a variable which can be used to provide increased stiffness, pushability and torqueability in some sections with greater flexibility in others. Additionally, composite cables according to the invention can incorporate additional elements normally not available in solid guide wires, such as optical, thermal or ultrasound imaging elements, therapeutic agent delivery catheters, and can take advantage of materials which are not readily adaptable to prior art catheter or guide wire designs incorporating a primary wire structured element. FIGS. 14a and 14b illustrate a further variable available because of the invention; the exterior wrapped cover 56 can be wound at greater or lesser intervals 60 along the outside to provide variations in the torqueability and stiffness of the composite cable. Also, the thickness and width of the wrapping cover 56, as well as its material composition along the composite guide wire 58, can offer further capabilities for customizing the design for various applications. These advantages can be combined with the benefits of shape memory or super-elastic alloys to create guidewires and other devices with heretofore unavailable capabilities.

FIG. 15 illustrates a cross-section of a micro-cable according to the invention which has at least one overall exterior sheath to contain the micro-cable. The micro-cable may be made of one or more multiple strand elements which may further include twisted or longitudinal strands within their construction. The sheath may also be used to control the torqueability characteristics of the cable and as discussed in copending application, Ser. No 08/986,004, the sheath may be multi-layered with different materials in order to provide a graduated bending and stiffness characteristic over the length of the cable.

Figure 23:
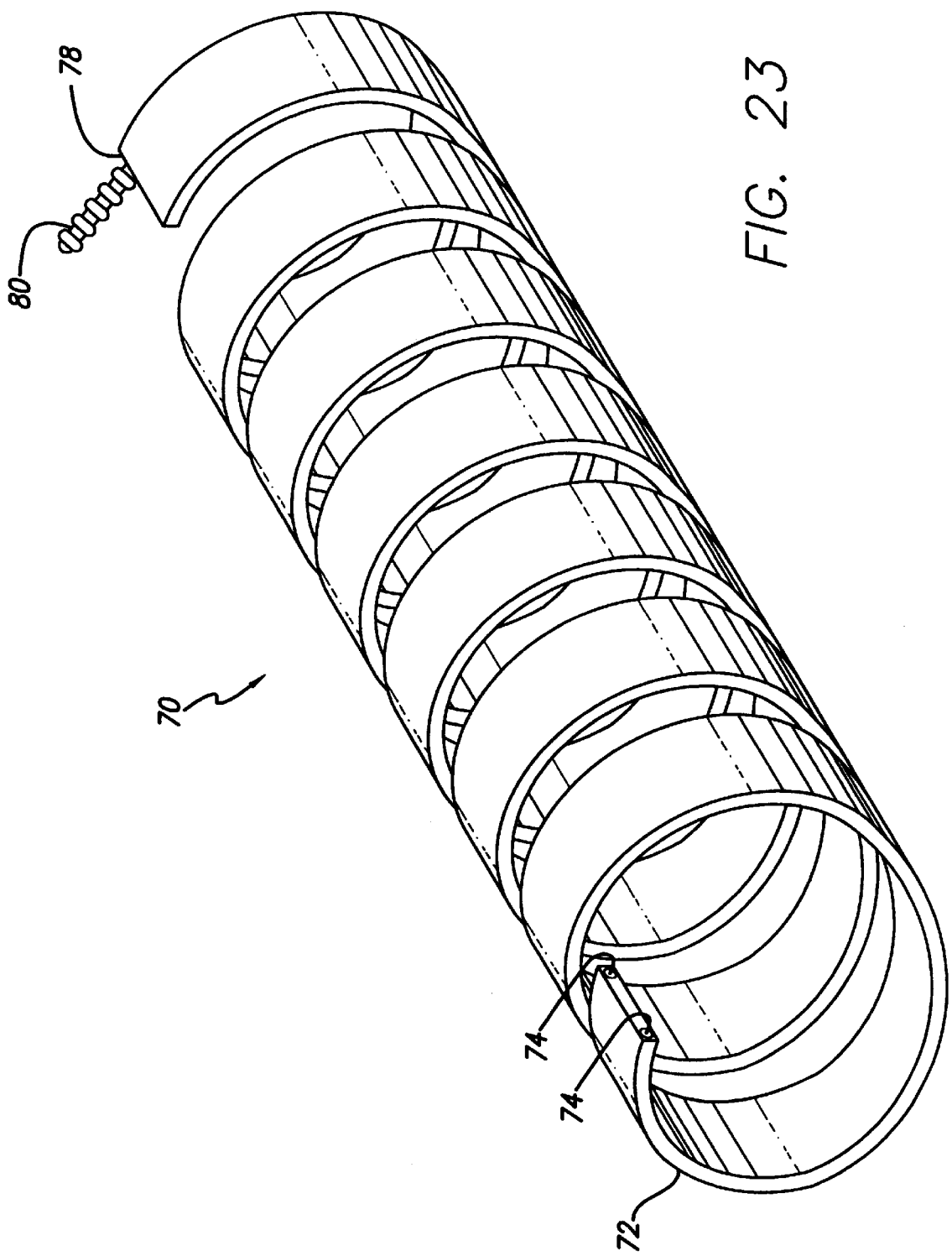
FIG. 23 is a perspective view of a final form of a helical superelastic collagen coated stent according to the principles of the invention.

FIGS. 17 to 23 illustrate a superelastic collagen coated stent that can advantageously be formed from one or more strands or micro-cables of such strands as described above. The superelastic collagen coated stent 70 can be compressed to a narrow thickness as illustrated in FIGS. 18B, 20B and 22B, and can be expanded at the site to be treated to the form of the superelastic collagen coated stent ribbon or tape forming a helical structure 72 illustrated in FIG. 23. The superelastic collagen coated stent comprises one or more groups of flexible strands 74 of superelastic, shape memory material, disposed within a tube 76 of collagen, forming a superelastic structure within the collagen tube that can be compressed along the width and length of the stent structure, to allow the stent structure to be pushed through a microcatheter or cannula. Alternatively, the tube may also be made of another suitable material that is preferably biocompatible, and may be a polymer material such as a thermoplastic or elastomer, or other similar materials, for example, that preferably can be loaded with a therapeutic agent for treatment of the desired site in the vasculature. As is illustrated in FIG. 23, when deployed, in a helical configuration, with a ribbon cross-section, a closed pitch is achieved, providing a collagen tube in contact with the vessel wall. The proximal end 78 of the stent preferably includes a stem 80, grippable by a shape memory collar as described above, to be detachable from a pusher member when delivered at the site in the vasculature to be treated. The stent structure can be manufactured by producing the inner superelastic structure, compressing the structure, sliding it into a collagen tube, and allowing the inner superelastic structure to expand and flatten the tube into a ribbon.

The collagen tube of the superelastic collagen coated stent is preferably loaded with a therapeutic agent or drug, such as to reduce or prevent restenosis and thrombosis in the vessel being treated, for example. The collagen tube of the superelastic collagen coated stent is preferably loaded with a therapeutic agent or drug, such as antiplatelets, antithrombins, cytostatic and antiproliferative agents such as are well known in the art, for example, to reduce or prevent restenosis in the vessel being treated. While such therapeutic agents have been used to prevent or treat restenosis and thrombosis, they are provided by way of example and are not meant to be limiting, as other therapeutic drugs may be developed which are equally applicable for use with the present invention.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A superelastic collagen coated stent for use in interventional therapy and vascular surgery, comprising in combination:
   a collagen tube; and
   a multi-stranded micro-cable disposed within said collagen tube, said multi-stranded micro-cable being formed from a plurality of flexible strands of a resilient shape memory material, said micro-cable including at least one radiopaque strand to provide a radiopaque marker.

2. The superelastic collagen coated stent of claim 1, wherein said combination of a collagen tube and a multi-stranded micro-cable forms a ribbon forming the structure of said stent.

3. The superelastic collagen coated stent of claim 2, wherein said ribbon is configured to have a helical shape.

4. The superelastic collagen coated stent of claim 1, wherein said a multi-stranded micro-cable has a sinusoidal shape.

5. The superelastic collagen coated stent of claim 1, comprising a plurality of said multi-stranded micro-cables disposed within said collagen tube.

6. The superelastic collagen coated stent of claim 1, wherein said at least one radiopaque strand comprises an axially disposed radiopaque wire.

7. The superelastic collagen coated stent of claim 1 wherein said plurality of flexible strands of a resilient material are comprised of a super-elastic material.

8. The superelastic collagen coated stent of claim 7 wherein said super-elastic material comprises a nickel titanium alloy.

9. The superelastic collagen coated stent of claim 1 wherein said shape memory material further comprises a nickel-titanium alloy.

10. The superelastic collagen coated stent of claim 1 wherein said shape memory material further comprises a shape memory polymer.

11. The superelastic collagen coated stent of claim 1 wherein said plurality of flexible strands further comprises a plurality of flexible strands twisted about a central core wire, at least one of said twisted strands comprising a radiopaque strand.

12. The superelastic collagen coated stent of claim 1 wherein said plurality of flexible strands further comprises a plurality of flexible strands twisted about a central core wire, said central core wire being made of a radiopaque material.

13. The superelastic collagen coated stent of claim 1 wherein said radiopaque strand comprises a platinum strand.

14. The superelastic collagen coated stent of claim 1 wherein said radiopaque strand comprises a gold strand.

15. The superelastic collagen coated stent of claim 1 wherein said radiopaque strand comprises a tungsten strand.

16. The superelastic collagen coated stent of claim 1 wherein said at least one radiopaque strand comprise a plurality of strands of said micro-cable, at least one of said plurality of radiopaque strands arrayed in the outer twisted strands of said cable.

17. The superelastic collagen coated stent of claim 1, wherein said collagen tube is loaded with a therapeutic agent.

18. A superelastic collagen coated stent for use in interventional therapy and vascular surgery, comprising in combination:

a multi-stranded micro-cable, said multi-stranded micro-cable being formed from a plurality of flexible strands of a resilient material, said micro-cable including at least one radiopaque strand to provide a radiopaque marker;

a sheath to constrain said strands of said micro-cable about a longitudinal axis; and said multi-stranded micro-cable and sheath being disposed within a collagen tube.

19. The superelastic collagen coated stent of claim 18 wherein at least one of said strands comprises a shape memory material.

20. The superelastic collagen coated stent of claim 19 wherein said shape memory material comprises a nickel titanium alloy.

21. The superelastic collagen coated stent of claim 18 wherein at least one of said strands comprises a super-elastic material.

22. The superelastic collagen coated stent of claim 21 wherein said superelastic material comprises a nickel titanium alloy.

23. The superelastic collagen coated stent of claim 18 wherein said sheath comprises a containment strand wound about said longitudinal strands.

24. The superelastic collagen coated stent of claim 18 further comprising an outer flexible sheath of low friction material.

25. The superelastic collagen coated stent of claim 18 wherein said sheath comprises a heat shrinkable plastic tube.

26. The superelastic collagen coated stent of claim 18 wherein said plurality of flexible strands of a resilient material are comprised of a super-elastic material.

27. The superelastic collagen coated stent of claim 26 wherein said superelastic material comprises a nickel titanium alloy.

28. The superelastic collagen coated stent of claim 18 wherein said plurality of flexible strands of a resilient material are comprised of a shape memory material.

29. The superelastic collagen coated stent of claim 28 wherein said shape memory material further comprises a nickel-titanium alloy.

30. The superelastic collagen coated stent of claim 28 wherein said shape memory material further comprises a shape memory polymer.

31. The superelastic collagen coated stent of claim 18 wherein said radiopaque strand comprises a platinum strand.

32. The superelastic collagen coated stent of claim 18 wherein said radiopaque strand comprises a gold strand.

33. The superelastic collagen coated stent of claim 18 wherein said radiopaque strand comprises a tungsten strand.

34. The superelastic collagen coated stent of claim 18 wherein said at least one radiopaque strand comprise a plurality of strands of said micro-cable.

35. The superelastic collagen coated stent of claim 18, wherein a plurality of flexible strands are twisted about a longitudinal axis, at least one of said twisted strands being of a radiopaque material.

* * * * *

UNITED STATES PATENT AND TRADEMARK OFFICE
CERTIFICATE OF CORRECTION

PATENT NO. : 6,241,691 B1　　　　　　　　　　　　　　　　　　　　Page 1 of 1
DATED : June 5, 2001
INVENTOR(S) : David A. Ferrera, Peter Wilson It is certified that error appears in the above-identified patent and that said Letters Patent is hereby corrected as shown below:

<u>Title page,</u>
FOREIGN PATENT DOCUMENTS, add the following:
-- 0 747 014 A1　　12/1996　　EP
0 743 047 A2　　11/1996　　EP
197 04 269 A1　　8/1997　　PCT --.

OTHER PUBLICATIONS, add the following:
-- International Search Report, Dated April 6, 1999 --.

<u>Column 7,</u>
Lines 18, 28, & 39, change "18-18, 20-20 & 22-22" respectively, to read -- 18A-18A, 20A-20A, & 22A-22A --.

Signed and Sealed this

Fifteenth Day of January, 2002

Attest:

JAMES E. ROGAN
*Attesting Officer*　　*Director of the United States Patent and Trademark Office*